United States Patent
Marquis (12)

(10) Patent No.: US 6,350,773 B1
(45) Date of Patent: Feb. 26, 2002

(54) THERAPEUTIC COMBINATIONS OF (S)-2-(BENZYLAMINO-METHYL)-2,3,8, 9,-TETRAHYDRO 7H-1,4-DIOXINO{2, 3-E}INDOL-8-ONE AND NEUROLEPTICS FOR THE TREATMENT OR PREVENTION OF PSYCHOTIC DISORDERS

(75) Inventor: Karen L. Marquis, Yardley, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/728,994

(22) Filed: Dec. 4, 2000

Related U.S. Application Data

(60) Provisional application No. 60/240,908, filed on Dec. 10, 1999, now abandoned.

(51) Int. Cl.[7] .............................................. A61K 31/40
(52) U.S. Cl. ...................................................... 514/411
(58) Field of Search ......................................... 514/411

(56) References Cited

U.S. PATENT DOCUMENTS 5,633,376 A     5/1997   Thurkauf et al. ............ 544/360
5,756,532 A  *  5/1998   Stack et al. .................. 514/411

FOREIGN PATENT DOCUMENTS

WO     WO9843646     10/1998

OTHER PUBLICATIONS

Windholz et al., Editor–in–Chief, The Merk Index, An Encyclopedia of Chemicals, Drugs, and Biologicals, 10th Edition, pp. 662 and 663, No. 4480, 1983.*

Lindenmayr, J.P. Acta Psychiatrica Scand. (supp. 388) 15–19, (1995–91).

K. Svensson et al., Neuropharmacology, 32(10), 1037–1045 (1993).

T.H. Svensson et al., *Schizophrenia Res.*, 9(2,3), p. 253 (1993).

Filip et al., Psychiatry Res., 41, 9–16 (1992).

* cited by examiner

*Primary Examiner*—Dwayne C. Jones
(74) *Attorney, Agent, or Firm*—Steven R. Eck

(57) ABSTRACT

Therapeutic combinations useful in the treatment or prevention of psychotic disorders, to pharmaceutical compositions containing said combinations, and to their use in the treatment or prophylaxis of prevention disorders are provided.

12 Claims, 3 Drawing Sheets

AGENT LACKS CATALEPTOGENIC POTENTIAL IN RATS

AGENT POTENTLY ANTAGONIZES d-AMPHETAMINE-INDUCE HYPERACTIVITY IN MICE

THERAPEUTIC COMBINATIONS OF (S)-2-(BENZYLAMINO-METHYL)-2,3,8,9,-TETRAHYDRO 7H-1,4-DIOXINO{2,3-E}INDOL-8-ONE AND NEUROLEPTICS FOR THE TREATMENT OR PREVENTION OF PSYCHOTIC DISORDERS

This application claims the benefit of U.S. Provisional Application No. 60/240,908, filed Dec. 10, 1999 now abandoned.

FIELD OF THE INVENTION

The present invention relates to therapeutic combinations of (S)-2-(benzylaminomethyl)-2,3,8,9-tetrahydro-7H-1,4-dioxin[2,3-e]indol-8-one, a partial agonist of the dopamine D2/D3 receptors, and antipsychotic agents, for the treatment or prophylaxis of psychotic disorders, to pharmaceutical compositions containing said combinations, and to their use in the treatment or prophylaxis of psychotic disorders.

BACKGROUND OF THE INVENTION

Psychoses are serious mental illnesses characterized by defective or lost contact with reality. These disorders are characterized by a variety of symptoms which are classified as positive symptoms (disordered thought, hallucinations, and delusions), negative symptoms (social withdrawal and unresponsiveness), and cognitive deficits.

Neuroleptics or antipsychotics can be used to treat schizophrenia and other related psychotic disorders by blocking the dopaminergic neurotransmission in the central nervous system. Neuroleptics are used widely to treat the "positive" symptoms of schizophrenia. However, many of these drugs are not considered to be effective for the treatment of "negative" symptoms of schizophrenia and may in fact exacerbate these symptoms because of the dopaminergic blockade associated with their mechanism of action. Cognitive deficits associated with schizophrenia, such as distractability, and executive skills such as a working memory and ability to plan, are also believed to be negatively effected by the blockade of dopamine receptors.

In addition, these neuroleptics have important side effects such as akathisia, dystonia, Parkinsonism dyskinesia and late dyskinesia and the like, which are caused by blocking the dopaminergic neurotransmission.

Anticholinergic agents such as Cogentin®, have been used to reduce Parkinson-like side effects, but also cause side effects such as mental and/or physical impairment, tachycardia, dysuria and gastrointestinal symptoms.

Some partial dopamine agonists with relatively high intrinsic activity have been shown to have effectiveness against the negative symptoms of schizophrenia. It has been hypothesized that in this respect, some intrinsic activity is desirable to optimize the treatment of negative symptoms while minimizing side effects. Lindenmayer, J. P., *Acta Psychiatrica Scand*. 1995:91 (supp. 388):15–19.

However, with increasing intrinsic activity, levels of dopamine transmission are higher and thus, positive symptoms may be less effectively treated.

It has been found that partial dopamine agonists having moderate to high intrinsic activity, such as preclamol, pramipexole and terguride have been useful in reversing the side effects of traditional neuroleptics. These reports indicate that higher intrinsic activity leads to greater effectiveness in alleviating motor dysfunction-related side effects. Svensson, et al., *Neuropharmacology*, 32(10):1037–1045 (1993).

New combination drug therapies may be useful for treatment of patients. It is greatly desired to optimize the beneficial properties of both drugs, while minimizing the side effects associated with the drugs when given alone. Applicants have found useful therapeutic combination for the treatment of psychotic disorders.

DETAILED DESCRIPTION OF THE INVENTION

Figure 1:
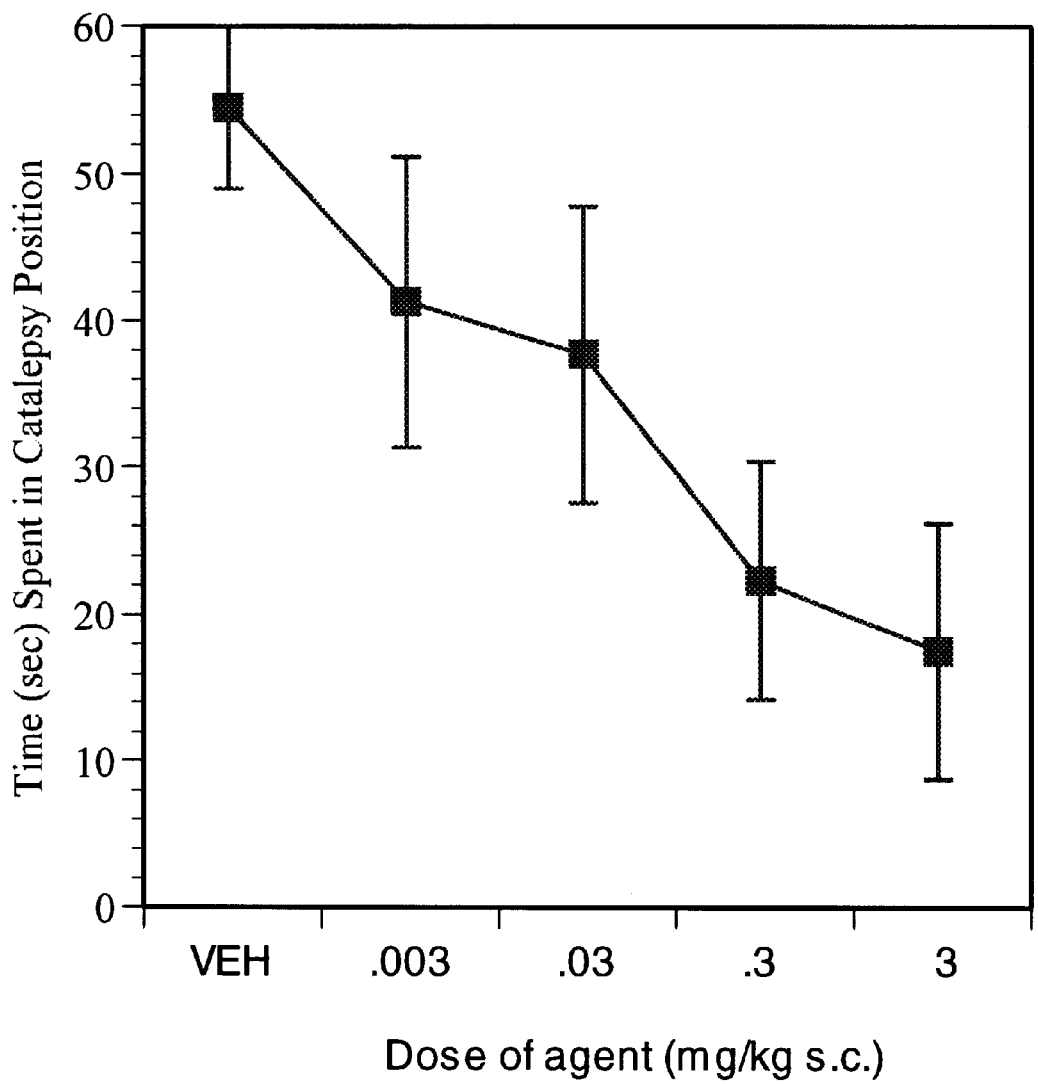
FIG. 1 is a schematic representation of the effect of (S)-2-(benzylaminomethyl)-2,3,8,9-tetrahydro-7H-1,4-dioxino[2,3-e]indol-8-one (agent) on haloperidol-induced catalepsy in rats at 60 minutes after drug treatment, the time point of greatest reversal as measured by seconds spent in catelepsy over a dose range of 0.003 to 3 mg/kg s.c. of agent. The data are means±SEM.

In accordance with the present invention is provided a composition comprising (S)-2-(benzylamino-methyl)-2,3,8,9-tetrahydro-7H-1,4-dioxino[2,3-e]indol-8-one, or pharmaceutical salts thereof, and one or more antipsychotic agents.

(S)-2-(Benzylamino-methyl)-2,3,8,9-tetrahydro-7H-1,4-dioxino[2,3-e]indol-8-one, a D2 partial agonist, is disclosed in U.S. Pat. No. 5,756,532. (S)-2(Benzylamino-methyl)-2,3,8,9-tetrahydro-7H-1,4-dioxino[2,3-e]indol-8-one, as used herein, includes pharmaceutical salts thereof, unless otherwise indicated.

Pharmaceutically acceptable salts include acid addition salts such as hydrochloric, fumaric, maleic, citric or succinic.

The term antipsychotic agent or neuroleptic agent includes those antipsychotics which work as a full antagonist of the dopamine D2 receptor and include both typical and atypical antipsychotics. Representative antipsychotic agents that are commercially available or known to those skilled in the art and include, but are not limited to:

Chlorpromazine, or 2-chloro-N,N-dimethyl-10H-phenothiazine-10-propanamine, is described in U.S. Pat. No. 2,645,640, which is incorporated by reference herein in its entirety.

Mesoridazine, or 10-[2-(1-methyl-2-piperidinyl)ethyl]-2-(methylsulfinyl)-10H-pheno-thiazine is described in U.S. Pat. No. 3,084,161, which is incorporated by reference herein in its entirety.

Thioridazine, or 10-[2-(1 -methyl-2-piperidinyl)ethyl]-2-(methylthio)-10H-phenothiazine is described in *Collect. Czech. Chem. Commun.*, 1990,55,1586–1601, which is incorporated by reference herein in its entirety.

Fluphenazine, or 4-[3-[2-(trifluoromethyl)-10H-phenothiazin-10-yl]propyl]-1-piperazineethanol is described in GB 829,246, which is incorporated by reference herein in its entirety.

Trifluoperazine, or 10-[3-(4-methyl-1-piperazinyl)-propyl]-2-(trifluoro-methyl)-10H-phenothiazine is described in GB 813,861 which is incorporated by reference herein in its entirety.

Perphenazine, or 4-[3-(2-chloro-10H-phenothiazin-1-yl) propyl]-1-piperazine-ethanol, is described in U.S. Pat. No. 2,766,235, which is incorporated by reference herein in its entirety.

Clozapine, or 8-chloro-11-(4-methyl-1-piperazinyl)-5H-dibenzo[b,e]-[1,4]-diazepine is described in U.S. Pat. No. 3,539,573, which is incorporated by reference herein in its entirety.

Haloperidol, or 4-[4-(4-chlorophenyl)-4-hydroxy-1-piperidinyl]-1-(4-fluorophenyl)-1-butanone is described in U.S. Pat. No. 3,438,991, which is incorporated by reference herein in its entirety.

Loxapine, or 2-chloro-11-(4-methyl-1-piperazinyl)-dibenz[b,f][1,4]oxazepine is described in U.S. Pat. No. 3,546,226, which is incorporated by reference herein in its entirety.

Molindone, or 3-ethyl-1,5,6,7-tetrahydro-2-methyl-5-(4-morpholinylmethyl)-4H-indol-4-one, is described in U.S. Pat. No. 3,491,093, which is incorporated by reference herein in its entirety.

Thiothixene, or N,N-dimethyl-9-[3-(4-methyl-1-piperazinyl)-propylidene-9H-thioxanthene-2-sulfanamide is described in U.S. Pat. No. 3,310,553, which is incorporated by reference herein in its entirety.

Sulpiride, or 5-(aminosulfonyl)-N-[(1-ethyl-2-pyrolidinyl)methyl]-2-methoxybenzamide, is described in U.S. Pat. No. 3,342,826, which is incorporated by reference herein in its entirety.

Amisulpiride, or 4-amino-N-[(1-ethyl-2-pyrrolidin-yl) methyl]-5-(ethylsulfonyl)-2-methoxybezamide, is described in U.S. Pat. No. 4,401,822, which is incorporated by reference herein in its entirety.

Risperidone, or 3-[2-[4-(6-fluoro-1,2-benzisoxazol-3-yl) piperidino]-ethyl]imidazolidin-2-one, is described in U.S. Pat. No. 4,804,663, which is incorporated by reference herein in its entirety.

Seroquel, or 11-[4-[2-(2-hydroxyethoxy)ethyl]-1-piperazinyl]dibenzo[b,f]-[1,4]thiazepine, preparation is described in EP 240228, which is incorporated by reference herein in its entirety.

Olanzapine, or 2-methyl-4-(4-methyl-1-piperazinyl)-10H-thieno[2,3-b][1,5]-benzodiazepine, is described in U.S. Pat. No. 5,229,382, which is incorporated by reference herein in its entirety.

Administration of (S)-2-(benzylamino-methyl)-2,3,8,9-tetrahydro-7H-1,4-dioxino[2,3-e]indol-8-one in combination with one or more antipsychotic agents is useful for the treatment or prevention of psychotic disorders associated with altered neurotransmission activity of the dopaminergic system in the central nervous system such as schizophrenia, schizoaffective disorder, acute mania, and depression with psychotic features, while eliminating or minimizing certain side affects associated with said antipsychotics when taken alone such as akathisia, dystonia, Parkinsonism dyskinesia and late dyskinesia and the like.

This invention also provides a product comprising (S)-2-(benzylaminomethyl)-2,3,8,9-tetrahydro-7H-1,4-dioxino-[2,3-e]indol-8-one and an antipsychotic agent as a combined preparation for simultaneous, separate or sequential administration to treat a patient suffering from a psychotic disorder.

Combinations of (S)-2-(benzylamino-methyl)-2,3,8,9-tetrahydro-7H-1,4-dioxino[2,3-e]indol-8-one and one or more antipsychotics, hereinafter referred to as "combinations" may be administered simultaneously, in the same or different pharmaceutical formulation, or sequentially. Of course the timing of the sequential administration should preserve the advantageous effects of the combination and said timing can be determined by a skilled practitioner.

A therapeutically acceptable amount of the combination will be understood to be an amount which treats, inhibits, prevents or ameliorates one or more symptoms of the psychotic disorder in question, preferably with fewer side effects than those associated with the administration of the antipsychotic agent alone. The dosages of each of the drugs in the combination must be determined by a physician and will depend upon the specific psychotic disorder, as well as the size, age and response pattern of the patient. Dosage guidelines are provided here. For the combination, the dosage guideline for each of the drugs of the combination would be considered.

In general, suitable doses of (S)-2-(benzylamino-methyl)-2,3,8,9-tetrahydro-7H-1,4-dioxino[2,3-e]indol-8-one, range from about 0.5 mg per day to about 100 mg per day, and more preferably from about 1 to about 50 mg per day.

A suitable dose of antipsychotic agent will be in the range recommended by the manufacturer. The following guidelines are provided for some preferred antipsychotics of the present invention:

Chlorpromazine: from about 300 to about 800 mg per day;
Mesoridazine: from about 100 to about 400 mg per day;
Thioridazine: from about 200 to about 600 mg per day;
Fluphenazine: from about 2 to about 5 mg per day;
Trifluoperazine: from about 6 to about 20 mg per day;
Perphenazine: from about 8 to about 40 mg per day;
Clozapine: from about 300 to about 600 mg per day:
Haloperidol: from about 1 to about 20 mg per day;
Loxapine: from about 60 to about 100 mg per day;
Molindone: from about 15 to about 225 mg per day;
Thiothixene: from about 20 to about 30 mg per day;
Risperidone: from about 4 to about 20 mg per day;
Seroquel: from about 15 to about 750 mg per day; and
Olanzapine: from about 10 to about 20 mg per day.

While it is possible for the active ingredients of the combination to be administered as the raw chemical, it is preferable to present them as a pharmaceutical formulation. Pharmaceutical formulations according to the present invention comprise a combination according to the invention together with one or more pharmaceutically acceptable carriers or excipients and optionally other therapeutic agents. The carriers must be acceptable in the sense of being compatible with the other ingredients in the formula. When the individual components of the combination are administered separately, they are generally each presented as a pharmaceutical formulation.

A combination of (S)-2-(benzylamino-methyl)-2,3,8,9-tetrahydro-7H-1,4-dioxino-[2,3-e]indol-8-one and an antipsychotic agent may conveniently be presented as a pharmaceutical formulation in a unitary dosage form. A convenient unitary dosage formulation contains the active ingredients in amounts from 0.1 mg to 1 g each, for example 5 mg to 100 mg. Typical unit doses may, for example, contain about 0.5 to about 100 mg (S)-2-(benzylamino-methyl)-2,3,8,9-tetrahydro-7H-1,4-dioxino[2,3-e]indol-8-one, and preferably about 1 mg to about 50 mg of (S)-2-(benzylamino-methyl)-2,3,8,9-tetrahydro-7H-1,4-dioxin[2,3-e]indol-8-one.

Pharmaceutical formulations may be prepared as "patient packs" containing the whole course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, with a package insert directing the patient to the correct use of the invention is a desirable additional feature of this invention.

According to a further aspect of the invention, there is provided a patient pack comprising at least one active ingredient of the combination of the invention and an information insert containing directions on the use of the combination of the invention.

Formulations include those suitable for oral, rectal, nasal, topical (including transdermal, buccal and sublingual), vaginal or parenteral (including subcutaneous, intramuscular, intravenous and intradermal) administration. The formulations may be prepared by any methods well known in the art of pharmacy, for example, using methods such as those described in Gennaro et al., *Remington's Pharmaceutical Sciences* (18th ed., Mack Publishing Company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavouring agents and wetting agents.

Formulations suitable for oral administration may be presented as discrete units such as pills, tablets or capsules each containing a predetermined amount of active ingredient; as a powder or granules; as a solution or suspension. The active ingredient may also be present as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilized) condition requiring only the addition of the sterile liquid carrier, for example, water prior to use.

Formulations suitable for administration by nasal inhalation include fine dusts or mists which may be generated by means of metered dose pressurized aerosols, nebulisers or insufflators.

The compounds of the combination of the present invention may be obtained in a conventional manner by methods known in the art.

The following examples are intended for illustration only and are not intended to limit the scope of the invention in any way.

As shown by the following examples, side effects caused by treatment with haloperidol are influenced by concommitant treatment with (S)-2-(benzylamino-methyl)-2,3,8,9-tetrahydro-7H-1,4-dioxin[2,3-e]indol-8-one.

EXAMPLE 1

Tests for reversal of haloperidol-induced catalepsy in rats were conducted according to a variation of the methods of Svensson et al., *Neuropharmacology*, 1993, 32:1037–1045. Rats (200–250 g) were transported from the colony room to the experimental room and held there for the duration of the experiment. Haloperidol, dissolved in 0.25% Tween 80®, was administered to all animals at a dose of 3 mg/kg i.p. Sixty minutes later, (S)-2-(benzylamino-methyl)-2,3,8,9-tetrahydro-7H-1,4-dioxino[2,3-e]indol-8-one, also dissolved in 0.25% Tween 80®, was administered s.c. at 4 dose levels to 6 male Sprague-Dawley rats per dose level. A control group, assessed simultaneously with (S)-2-(benzylamino-methyl)-2,3,8,9-tetrahydro-7H-1,4-dioxino[2,3-e]indol-8-one treated groups, received a vehicle (VEH) injection of 0.25% Tween 80® at equal volumes (1 ml/kg). Animals were assessed for catalepsy at 30, 60, 90 and 120 minutes after drug administration by placing the animal's forepaws on a wooden cube (8×8×8 cm). The time that the animal remained with at least one of the forepaws on the cube was measured (maximum=60 sec). The righting reflex was then tested and used to discard sedated subjects. Data were analyzed using a two-factor analysis of variance with one repeated measure. A subsequent least significant difference from control test ($p<0.05$) was used to determine the minimal effective dose (MED) for reversing haloperidol-induced catalepsy and to determine time of onset. A trend test was then used to determine at which time points (if any) there was a dose-related effect. From these time points the point showing the greatest degree of reversal (having the lowest catalepsy scored) was used to calculate $ED_{50}$ (dose producing 50% reduction in maximal response) and 95% confidence intervals. This was done using nonlinear regression analysis followed by inverse prediction.

FIG. 1 is a schematic representation of the effect of (S)-2-(benzylamino-methyl)-2,3,8,9-tetrahydro-7H-1,4-dioxino[2,3-e]indol-8-one (agent) on haloperidol-induced catalepsy in rats at 60 minutes after drug treatment, the time point of greatest reversal. The data are means±SEM. As shown in the figure, a dose-dependent decrease in time spent in catalepsy position was observed. A MED of 0.3 mg/kg and an $ED_{50}$ of 0.08 mg/kg were calculated from these results.

EXAMPLE 2

Tests for cataleptogenic potential of (S)-2-(Benzylamino-methyl)-2,3,8,9-tetrahydro-7H-1,4-dioxino[2,3-e]indol-8-one in rats were conducted by a method similar to that described in Example 1, except that haloperidol was not administered.

Figure 2:
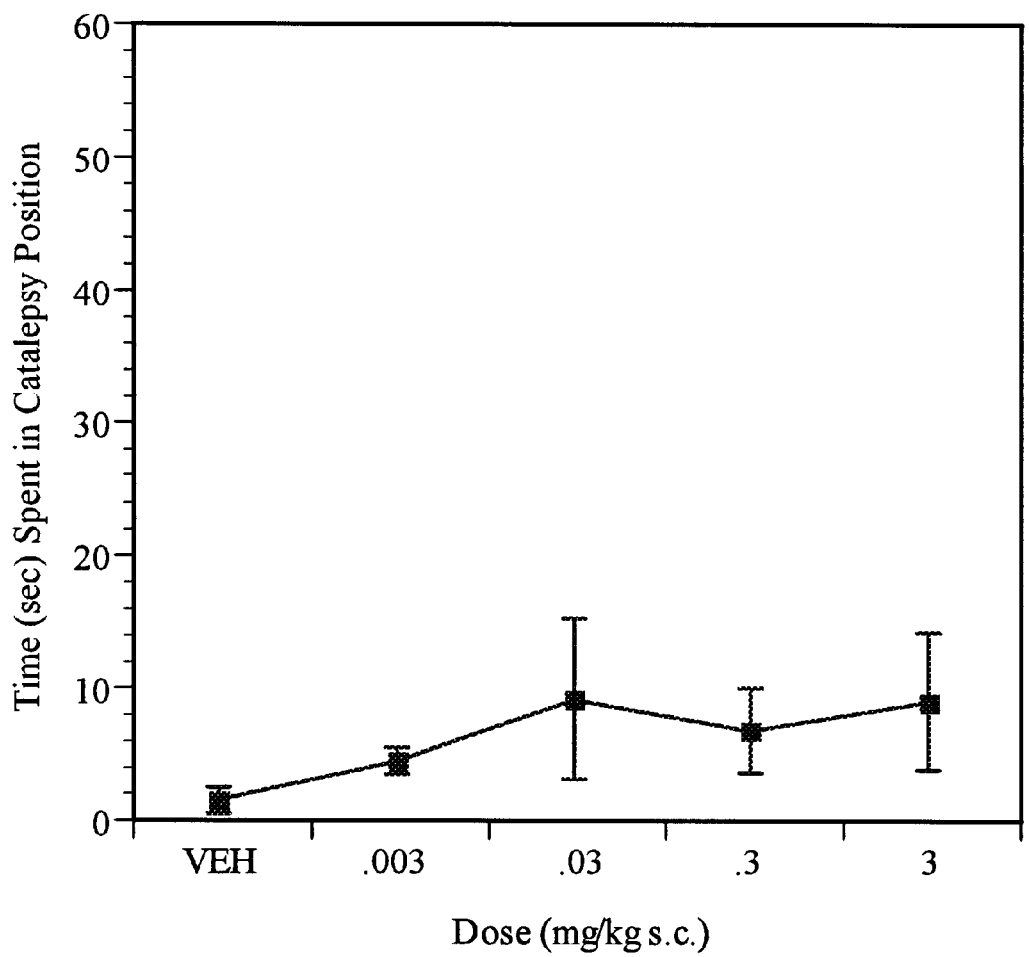
FIG. 2 is a schematic representation of the ability of (S)-2-(Benzylamino-methyl)-2,3,8,9-tetrahydro-7H-1,4-dioxino[2,3-e]indol-8-one (agent) to induce catalepsy in rats as measured by seconds spent in catelepsy catelepsy over a dose range of 0.003 to 3 mg/kg s.c. of agent. The data are means±SEM.

FIG. 2 is a schematic representation of the ability of (S)-2-(Benzylamino-methyl)-2,3,8,9-tetrahydro-7H-1,4-dioxino[2,3-e]indol-8-one (agent) to induce catalepsy in rats. The data are means±SEM. As shown in the figure, there is a lack of ability of the agent to induce significant catalepsy in rats over a dose range of 0.003 to 3 mg/kg s.c. at 60 min post dosing. Similar results were observed at the other time points tested.

EXAMPLE 3

The ability to antagonize amphetamine-induced hyperlocomotion was tested according to a modified version of the methods of Riffee and Wilcox, *Psychopharmacology*, 1985, 85:97–101. Mice (25–30 g) were transported from the colony room to the experimental room and held there for the duration of the experiment. The animals were habituated in the locomotor test chambers (an open field 8×8 in.) for 60 min prior to testing. Following the habituation period, d-amphetamine (2.5 mg/kg i.p., dissolved in distilled water) was administered to all animals. Fifteen minutes later, test compounds dissolved in 0.25% Tween 80® were administered s.c. at 8 dose levels to 8 mice per dose level. Control groups, assessed simultaneously with drug-treated groups, received vehicle at equal volumes (10 ml/kg). Immediately after administration of the test compound, animals were placed individually into the locomotor activity chambers. Activity was monitored for 30 minutes with lights on using Omnitech Digiscan® (Columbus, Ohio) infrared monitors. Each infrared beam break was counted by the automated system and totaled at 10 minute intervals. Horizontal activity counts collected between 10 and 20 min after the onset of the test session were subjected to a one-way analysis of variance followed by Student-Newman-Keuls test ($p<0.05$) to determine doses which were effective at antagonizing d-amphetamine-induced hyperlocomotion relative to the vehicle-treated control group. Mean horizontal activity counts were analyzed by nonlinear regression followed by inverse prediction to calculate the $ED_{50}$ (dose producing 50% reduction in activity) and 95% confidence intervals (CI) as well as slope and minimum activity level.

Figure 3:
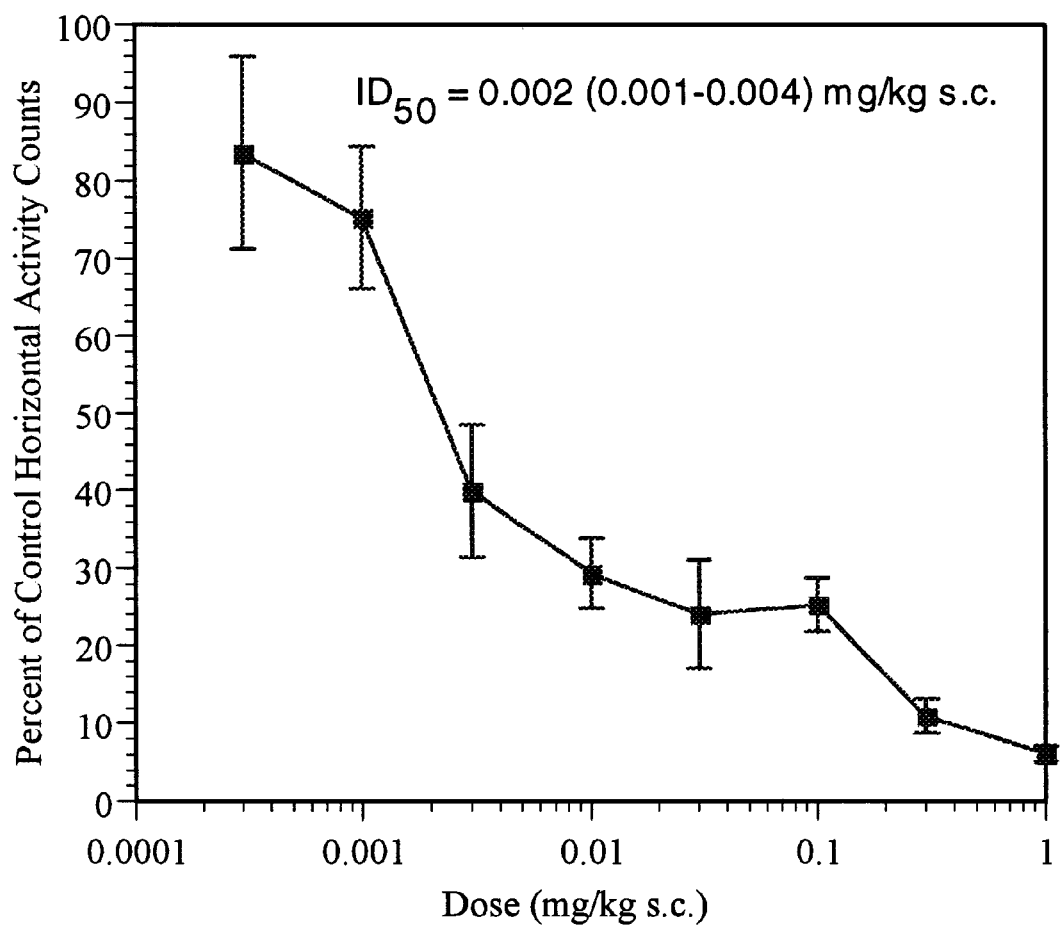
FIG. 3 is a schematic representation of the effect of (S)-2-(Benzylamino-methyl)-2,3,8,9-tetrahydro-7H-1,4-dioxino[2,3-e]indol-8-one (agent) to reverse d-amphetamine induced hyperactivity in mice. The data are expressed as a percentage of the activity level (horizontal activity counts) observed in mice treated with d-amphetamine alone for eight doses ranging from 0.0001 to 1 mg/kg s.c. of agent. The data are presented as means±SEM.

FIG. 3 is a schematic representation of the effect of (S)-2(Benzylamino-methyl)-2,3,8,9-tetrahydro-7H-1,4-dioxino[2,3-e]indol-8-one (agent) to reverse d-amphetamine induced hyperactivity in mice. The data are expressed as a percentage of the activity level observed in mice treated with d-amphetamine alone and are presented as means±SEM. As shown in the figure, a dose-dependent decreased in d-amphetamine-induced hyperactivity was observed. An $ED_{50}$ of 0.002 mg/kg was calculated from these results.

Thus, compositions of the present invention reduce side effects induced by haloperidol as modeled by catelepsy, while not diminishing the ability of haloperidol to treat positive symptoms of schizophrenia as modeled by the amphetamine-induced hyperactivity.

What is claimed is:

1. A composition comprising (S)-2-(Benzylamino-methyl)-2,3,8,9-tetrahydro-7H-1,4-dioxino{2,3-e}indol-8-one and an antipsychotic agent.

2. A pharmaceutical composition comprising (S)-2-(Benzylamino-methyl)-2,3,8,9-tetrahydro-7H-1,4-dioxino{2,3}indol-8-one, an antipsychotic agent, and one or more pharmaceutical carriers therefor.

3. A method of treating a patient suffering from a psychotic disorder comprising administering to said patient an effective amount of (S)-2-(Benzylamino-methyl)-2,3,8,9-tetrahydro-7H-1,4-dioxino{2,3-e}indol-8-one, in combination with an effective amount of an antipsychotic agent.

4. The method of claim 1 wherein the antipsychotic agent is an atypical antipsychotic.

5. The method of claim 1 wherein the antipsychotic agent is a typical antipsychotic.

6. The method of claim 1 wherein the antipsychotic agent is selected from the group consisting of chlorpromazine, mesoridazine, thioridazine, fluphenazine, trifluoperazine, perphenazine, clozapine, haloperidol, loxapine, molindone, thiothixene, risperidone, seroquel, and olanzapine.

7. The method of claim 1 wherein administration of the compounds is oral.

8. The method of claim 1 wherein the patient is suffering from schizophrenia.

9. The method of claim 1 wherein the patient is suffering from schizoaffective disorder.

10. The method of claim 1 wherein the patient is suffering from depression.

11. The method of claim 1 wherein the antipsychotic is administering in the amount of about 10 mg to about 1000 mg per day.

12. A patient pack comprising at least one active ingredient selected from (S)-2-(Benzylamino-methyl)-2,3,8,9-tetrahydro-7H-1,4-dioxin{2,3-e}indol-8-one and an antipsychotic agent, and comprising an information insert containing directions on the use of the active ingredient or active ingredients in a combination comprising (S)-2-(Benzylamino-methyl)-2,3,8,9-tetrahydro-7H-1,4-dioxin{2,3-e}indol-8-one and an antipsychotic.

* * * * *